United States Patent [19]

Cragoe, Jr. et al.

[11] 4,237,144

[45] Dec. 2, 1980

[54] 2,3-DIHYDRO-2,6,7-TRISUBSTITUTED-5-ACYLBENZOFURANS

[75] Inventors: Edward J. Cragoe, Jr.; William F. Hoffman, both of Lansdale, Pa.

[73] Assignee: Merck & Co., Inc., Rahway, N.J.

[21] Appl. No.: 50,852

[22] Filed: Jun. 21, 1979

[51] Int. Cl.$^3$ .................. A61K 31/425; C07D 285/10; C07D 307/83

[52] U.S. Cl. .................. 424/270; 424/275; 424/285; 260/346.22; 260/346.71; 260/346.73; 548/134; 549/60

[58] Field of Search ............ 260/346.22, 346.71, 260/346.73; 548/134; 549/60; 424/270, 275, 285

[56] References Cited

U.S. PATENT DOCUMENTS 4,087,542  5/1978  Cragoe, Jr. et al. ............ 424/275

Primary Examiner—Henry R. Jiles
Assistant Examiner—Bernard Dentz
Attorney, Agent, or Firm—Michael C. Sudol, Jr.; Harry E. Westlake, Jr.

[57] ABSTRACT

This invention relates to 2,3-dihydro-2,6,7-trisubstituted-5-acylbenzofurans, derivatives thereof and processes for their preparation. The novel benzofurans described herein have diuretic-saluretic, uricosuric and antihypertensive pharmacological activity.

11 Claims, No Drawings

2,3-DIHYDRO-2,6,7-TRISUBSTITUTED-5-ACYL-BENZOFURANS

BACKGROUND OF THE INVENTION

This invention relates to certain benzofurans having diuretic-saluretic, uricosuric and antihypertensive pharmacological activity. Further, this invention relates to processes for the preparation of such compounds; pharmacological compositions comprising such compounds; and to methods of treatment comprising administering such compounds and compositions to patients (both human and animal) for the alleviation of symptoms associated with electrolyte imbalance and fluid retention such as edema associated with hypertension.

The compounds of this invention may be represented by the following generic structure:

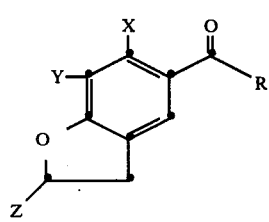

wherein
X is halo(chloro, fluoro, bromo or iodo) or methyl
Y is halo(chloro, fluoro, bromo or iodo) methyl or hydrogen
X and Y can be joined to form a hydrocarbylene chain containing from 3 to 4 carbon atoms, for example: 1,3-butadienylene:
R is aryl such a phenyl or mono or disubstituted phenyl wherein the substituent is halo, methyl trifluoromethyl or methoxy; aralkyl such as benzyl or mono or dinuclear substituted aralkyl wherein the substitutent is halo, methyl, methoxy or trifluoromethyl; or a heterocyclic group such as a 5 or 6 membered heterocyclic ring containing one or more atoms of oxygen, sulfur or nitrogen such as 3-, or 2-thienyl, 3 or 2-furyl, 1,2,5-thiadiazolyl or substituted heterocyclics as above wherein the substituent is halo or methyl.
Z is acetyl, aminomethyl, formyl, hydroxymethyl, dialkyl acetal and ethylene acetal.

The pharmacological studies show that the instant products are effective diuretic, saluretic and uricosuric agents which can be used in the treatment of conditions associated with electrolyte and fluid retention in the treatment of edema, hypertension, congestive heart failure and the like. These compounds are able to maintain the uric acid concentration in the body at pretreatment levels or to even effect a decrease in the uric acid concentration when administered in therapeutic dosages in conventional vehicles.

Many of the presently available diuretics and saluretics have a tendency upon administration to induce hyperuricemia which may precipitate uric acid or sodium urate or both in the body which may cause from mild to severe cases of gout. The instant compounds of this invention now provide an effective tool to treat those patients (which includes humans and animals) requiring diuretic and saluretic treatment without incurring the risk of inducing gout. In fact, when used in appropriate doses, the compounds of this invention function as uricosuric agents.

Thus it is an object of the present invention to provide the benzofurans of the above general description and to provide processes for preparation of such compounds. Further objects of this invention are to provide pharmaceutical compositions comprising such benzofurans and to provide methods of treatment comprising administering such compounds and compositions.

DETAILED DESCRIPTION OF THE INVENTION

For purposes of description, the benzofurans of the present invention (Formula I above) may be represented according to the following structural formula:

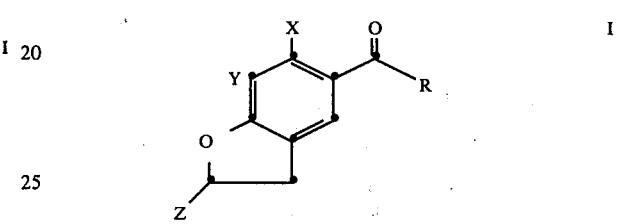

wherein X, Y, Z and R are as previously defined.

The preferred benzofurans of the present invention are those compounds of Formula I wherein X is halo, preferably chloro, or methyl and Y is halo, preferably chloro or methyl, and Z is acetyl, aminomethyl, formyl, or hydroxymethyl.

More preferred benzofurans of the present invention are those preferred compounds of Formula I wherein R is

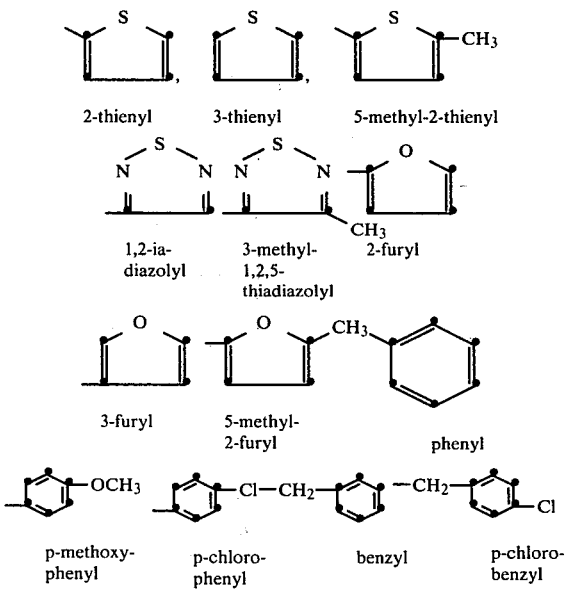

and X, Y and Z are as defined above.

Still more preferred benzofurans of the present invention are those compound of Formula II below:

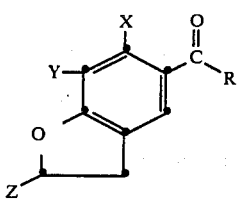

wherein
X is chloro and
Y is chloro, and
Z if formyl or hydroxymethyl
R is as defined for the more preferred benzofurans above.

A still more preferred aspect of the invention are those compounds of Formula II wherein X and Y are both chloro, Z is formyl or hydroxymethyl and R is:

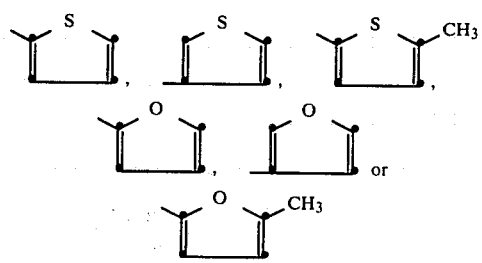

Several examples of specific compounds of this invention are:
6,7-Dichloro-2,3-dihydro-5-(2-thenoyl)benzofuran-2-carboxaldehyde
6,7-Dichloro-2,3-dihydro-5-(2-furoyl)benzofuran-2-carboxaldehyde 6,7-Dichloro-2,3-dihydro-5-(5-methyl-2-thenoyl)benzofuran-2-carboxaldehyde;
6,7-Dichloro-2,3-dihydro-5-(3-thenoyl)benzofuran-2-carboxaldehyde
6,7-Dichloro-2,3-dihydro-5-(3-furoyl)benzofuran-2-carboxaldehyde
6,7-Dichloro-2,3-dihydro-5-(5-methyl-2-furoyl)benzofuran-2-carboxaldehyde
6,7-Dichloro-2,3-dihydro-5-(1,2,5-thiadiazol-3-yl)benzofuran-2-carboxylic acid
6,7-Dichloro-2,3-dihydro-2-hydroxymethyl-5-(2-thenoyl)-benzofuran
6,7-Dichloro-2,3-dihydro-2-hydroxymethyl-5-(2-furoyl)-benzofuran
6,7-Dichloro-2,3-dihydro-2-hydroxymethyl-5-(3-thenoyl) benzofuran
6,7-Dichloro-2,3-dihydro-2-hydroxymethyl-5-(3-furoyl)-benzofuran
6,7-Dichloro-2,3-dihydro-2-hydroxymethyl-5-(5-methyl-2-furoyl)benzofuran
6,7-Dichloro-2,3-dihydro-2-hydroxymethyl-5-(5-methyl-2-thenoyl)benzofuran
6,7-Dichloro-2,3-dihydro-2-hydroxymethyl-5-(1,2,5-thiadiasol-3-yl)benzofuran
6,7-Dichloro-2,3-dihydro-5(2-thenoyl)benzofuran-2-ethylene-acetal
6,7-Dichloro-2,3-dihydro-5(2-thenoyl)benzofuran-2-dimethyl-acetal
2-Aminomethyl-6,7-dichloro-2,3-dihydro-5-(2-thenoyl)benzofuran
2-Acetyl-6,7-dichloro-2,3-dihydro-5-(2-thenoyl)benzofuran.

The preferred groups of compounds depicted above have especially good diuretic, saluretic, uricosuric and antihypertensive pharmacological activity.

The benzofurans of the present invention may be prepared essentially by the reaction scheme shown below:

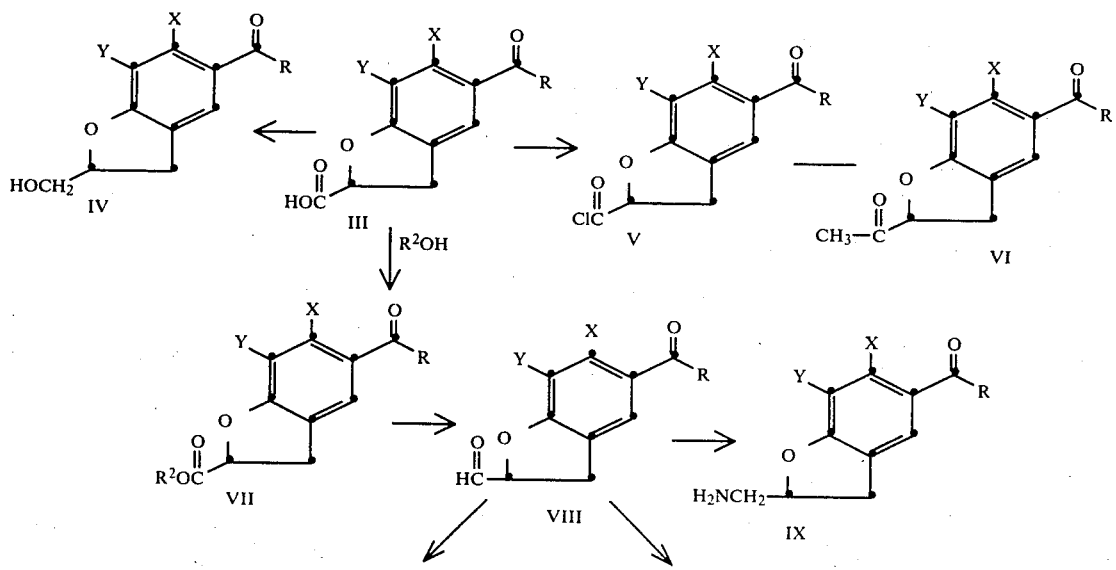

-continued

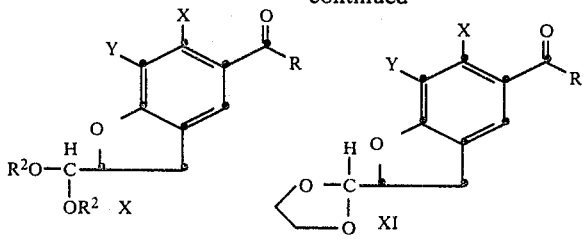

wherein X, Y and R are as defined and $R^2$ is lower alkyl ($C_{1-4}$).

In this reaction scheme, a 5, 6, 7-trisubstituted, 2,3-dihydrobenzofuran 2-carboxylic acid (III) is reduced to yield the corresponding hydroxy methyl compound (IV). Typically the reduction is carried out at 0° to 25° C. in tetrahydrofuran, ether or diglyme with borane as the reducing agent. The borane used may be a borane-tetrahydrofuran complex, a borane-methylsulfide complex with excess trimethylborate or it may be generated in situ from the reaction of sodium borohydride and boron trifluoride eitherate.

The benzofuran-2-carboxylic acid (III), is also the starting material for the synthesis of the corresponding 2-acetyl compound (VI). (III) is converted to the acid chloride (V) by treatment with an inorganic halide with or without a solvent at 25° to 100° C. Typically the organic halides employed are, thionyl chloride, phsophorus trichloride, or phosphorus pentachloride. The solvents usually employed are benzen or toluene. Coupling of the acid chloride (V) with an organometallic reagent in ether or benzene yields the methyl ketone derivatives (VI). Typically the organometallic reagents employed are lithium dimethylcuprate, lithium di-n-butylcuprate, dimethylzinc, diethylzinc, di-isoamylcadmium or di-n-butylcadmium. The temperature of the reaction depends upon the organometallic reagent used and can vary from −78° C. to 80° C. The ester (VII) is prepared from the acid (III) by treating the acid with an acidic catalyst in an excess of the alcohol, usually at the boiling point of the alcohol, for two to six hours. Typically catalysts are sulfuric acid, hydrogen chloride, p-toluenesulfonic acid or boron trifluoride etherate. Reduction of the ester (VII) at −50° C. to −70° C. with a complex metal hydride in tetrahydrofuran, toluene or ether yields the aldehyde derivative (VIII). Typical complex metal hydride reducing agents are, lithium aluminum hydride, sodium aluminum hydride, potassium aluminum hydride, sodium bis(2-methoxyethoxy)aluminum hydride, lithium tri-t-butyloxy-aluminum hydride and diisobutyl aluminum hydride. The aldehyde (VIII) is converted to its acetal (X) by treating it with the appropriate alcohol at 0°–80° C. with an acidic catalyst. Typically catalysts are, hydrogen chloride, calcium chloride cesium chloride, ammonium chloride, p-toluenesulfonic acid, hydrogen bromide, boron trifluoride etherate, malonic acid or selenium dioxide. The cyclic acetal (XI) is prepared by refluxing a benzene or toluene solution containing the aldehyde (VIII), with an excess of ethylene glycol and an acidic catalysis for three to twelve hours and collecting the water formed in a Dean-Stark apparatus. The typical catalysts are the same as used in the synthesis of (X).

Reductive amination of the aldehyde (VIII) yields the amino methyl derivative (IX). Typically the reaction is carried out at 25° C. from three to forty-eight hours in a methanol solution containing the aldehyde (VIII), ammonium acetate and sodium (or lithium) cyanohydridoborate.

The instant compounds disclosed herein contain asymmetric carbon atom at position 2 of the benzofuran ring. The enantiomers may be separated by methods well known to those skilled in the art. This invention, therefore, embraces not only the racemic benzofurans but also the optically active enantiomers. In general, the pure enantiomers are prepared starting with the pure enantiomeric carboxylic acids (III) rather than the racemic compounds. Several specific enantiomeric carboxylic acids (III) that are used are (+)6,7-dichloro-2,3-dihydro-5-(2-thenoyl)-benzofuran-2-carboxylic acid and (−)6,7-dichloro-2,3-dihydro-5-(2-thenoyl)-benzofuran-2-carboxylic acid, from which the enantiomeric derivatives (IV, VI, VIII, IX, X and XI) are synthesized.

Unexpectedly, the ratio of the two pharmacodynamic activities, i.e., saluretic-diuretic and uricosuric, is not necessarily the same in each enantiomer. In fact, in some instances, one property lies almost entirely in the (+)-enantiomer while the other lies in the (−)-enantiomer. For example, racemic 6,7-dichloro-2,3-dihydro-5-(2-thenoyl)benzofuran-2-carboxaldehyde exhibits both potent saluretic-diurectic and uricosuric activity. The (+)-enantiomer possesses marked saluretic-diuretic activity with very little uricosuric effects while the reverse is true for the (−)-enantiomer. This unique situation permits a selection of any desired ratios of the two properties by selection of the appropriate ratio of the two enantiomers. For example when various isomeric ratios of the two enantiomers of 6,7-dichloro-2,3-dihydro-5-(2-thenoyl)benzoforan- 2-carboxyaldehyde are administered orally to chimpanzees in a total dose of 5 mg./kg., the following observations are made.

|            | % of Isomer | | saluresis-diuresis | Uricosuric |
|---|---|---|---|---|
|            | + | − |  |  |
|            | 100 | 0 | very marked | marginal |
|            | 75 | 25 | very marked | weak |
| (racemate) | 50 | 50 | marked | modest |
|            | 25 | 75 | good | strong |
|            | 12.5 | 87.5 | modest | marked |
|            | 0 | 100 | marginal | very marked |

Although diuretics are often life-saving because of the above beneficial therapeutic effects, most of them have the disadvantage of causing the excretion of appreciable amounts of potassium ions. When an excessive loss of potassium ions occurs, a severe muscular weakness and feeling of extreme physical exhaustion results. The patient eliminates the unwanted sodium ions due to the action of the diuretic drugs but the undesired elimination of the potassium ions produces an imbalance that should not be allowed to persist.

This invention also involves co-administration of a dihydrobenzofuran derivative with a pyrazinoylguanidine either in the form of a salt and/or as a mixture with a hydrochloride salt of pyrazinoylguanidine, to thereby prevent the elimination of excessive amounts of potassium ions without altering or actually increasing the amount of sodium ions that are eliminated.

To achieve the beneficial results of this invention, the preferred pyrazinoylguanidine compound is N-amidino-3,5-diamino-6-chloropyrazinecarboxamide (amiloride) or its hydrochloride salt (amiloride hydrochloride) which is described in the literature and patented arts.

Another advantage of the N-amidino-3,5-diamino-6-chloropyrazinecarboxamide salts of the dihydrobenzofurancarboxylic acid diuretics is their insolubility which makes the salts gastrointestinal absorption slower and more gradual providing a chemical method of achieving the same effect as microencapsulation.

The examples which follow illustrate the benzofuran products of the present invention and the methods by which they are prepared. However, the examples are illustrative only and it will be apparent to those having ordinary skill in the art that all the products embraced by the above given description of the present invention may also be prepared in an analogous manner by substituting the appropriate starting materials for those set forth in the examples.

EXAMPLE 1

(±)6,7-Dichloro-2,3-dihydro-2-hydroxymethyl-5-(2-thenoyl)-benzofuran

To a stirred solution of (±) 6,7-dichloro-2,3-dihydro-5-(2-thenoyl)benzofuran-2-carboxylic acid (3.4 g., 0.01 mole) in tetrahydrofuran (50 ml.) at 0° C. is added the borane-tetrahydrofuran complex (25 ml., 0.00625 mole) over a one-half hour period. The reaction solution is stirred one hour at 0° C. and 18 hours at 25° C. The reaction solution is diluted with aqueous sodium bicarbonate (50 ml.) and the water layer is separated and the extracted twice with ether (two 20 ml. portions). The organic layers are combined, washed with brine (two 10 ml. portions), dried over magnesium sulfate and the solvents distilled at reduced pressure. The (±)6,7-dichloro-2,3-dihydro-2-hydroxymethyl-5-(2-thenoyl)-benzofuran is purified by column chromatography on silica gel (95% benzene-5% methanol) and melts at 65°-8° C. (yield 21%).

Elemental analysis for $C_{14}H_{10}Cl_2O_3S$; Calc.: C, 51.07; H, 3.06. found: C, 51.19; H, 3.21.

EXAMPLE 2

Where in Example 1, there is substituted for (±) 6,7-dichloro-2,3-dihydro-5-(2-thenoyl)benzofuran-2-carboxylic acid an equivalent amount of (±)6,7-dichloro-2,3-dihydro-5(2-furoyl)benzofuran-2-carbooxylic acid,, (±)6,7-dichloro-2,3-dihydro-5-(3-thenoyl)benzofuran-2-carboxylic acid, (±)6,7-dichloro-2,3-dihydro-5-(5-methyl-2-thenoyl)-benzofuran-2-carboxylic acid, (±)6,7-dichloro-2,3-dihydro-5-(5-methyl-2-furoyl)benzofuran-2-carboxylic acid, (±)2,3-dihydro-6,7-dimethyl-5-(2-thenoyl)benzofuran-2-carboxylic acid, (±)2,3-dihydro-6,7-dimethyl-5-(2-furoyl)benzofuran- 2-carboxylic acid, (±)6-chloro-2,3-dihydro-7-methyl-5-(2-thenoyl)benzofuran-2-carboxylic acid or (±)6-chloro-2,3-dihydro-7-methyl-5-(2-furoyl)benzofuran-2-carboxylic acid, the following compounds of this invention are obtained, respectively:

(±)6,7-dichloro-2,3-dihydro-2-hydroxymethyl-5-(2-furoyl) benzofuran;
(±)6,7-dichloro-2,3-dihydro-2-hydroxymethyl-5-(3-thenoyl) benzofuran;
(±)6,7-dichloro-2,3-dihydro-2-hydroxymethyl-5-(5-methyl-2-thenoyl)benzofuran;
(±)6,7-dichloro-2,3-dihydro-2-hydroxymethyl-5-(5-methyl-2-furoyl)benzofuran;
(±)2,3-dihydro-2-hydroxymethyl-6,7-dimethyl-5-(2-thenoyl)-benzofuran;
(±)2,3-dihydro-2-hydroxymethyl-6,7-dimethyl-5-(2-furoyl)-benzofuran;
(±)6-chloro-2,3-dihydro-2-hydroxymethyl-7-methyl-5-(2-thenoyl)benzofuran;
(±)6-chloro-2,3-dihydro-2-hydroxymethyl-7-methyl-5-(2-furoyl)-benzofuran.

EXAMPLE 3

(+)6,7-Dichloro-2,3-dihydro-2-hydroxymethyl-5-(2-thenoyl)-benzofuran

Where in Example 1 there is substituted for (±) 6,7-dichloro-2,3-dihydro-5-(2-thenoyl)benzofuran-2-carboxylic acid an equivalent amount of (+)6,7-dichloro-2,3-dihydro-5-(2-thenoyl)benzofuran-2-carboxylic acid, there is produced an equivalent amount of (+)6,7-dichloro-2,3-dihydro-2-hydroxymethyl-5-(2-thenoyl)-benzofuran.

EXAMPLE 4

(−)6,7-Dichloro-2,3-dihydro-2-hydroxymethyl-5-(2-thenoyl)-benzofuran

Where in Example 1 there is substituted for (±)6,7-dichloro-2,3-dihydro-5-(2-thenoyl)benzofuran-2-carboxylic acid an equivalent amount of (−)6,7-dichloro-2,3-dihydro-5-(2-thenoyl)benzofuran-2-carboxylic acid, there is produced an equivalent amount of (−)6,7-dichloro-2,3-dihydro-2-hydroxymethyl-5-(2-thenoyl)-benzofuran.

EXAMPLE 5

(±)6,7-Dichloro-2,3-dihydro-5-(2-thenoyl)benzofuran-2-carboxaldehyde

To a stirred solution of (±)methyl-6,7-dichloro-2,3-dihydro-5-(2-thenoyl)benzofuran-2-carboxylate (3.57 g., 0.01 mole) in tetrahydrofuran (50 ml.) at −70° C. is added a solution of "Red-Al" (1.5 g., 0.0107 mole) in tetrahydrofuran (10 ml.) over a ten minute period. The reaction solution is stirred one hour at −70° C. and then quenched with 20% sulfuric acid (10 ml.). The water layer is separated and extracted twice with tetrahydrofuran (10 ml.). The organic layers are combined, washed with brine (two 5 ml. portions), dried over magnesium sulfate and the tetrahydrofuran distilled at reduced pressure. The residue is dissolved in n-butyl chloride (50 ml.) and added to a solution of sodium bisulfite (6 g.) in warm water (10 ml.). The mixture is stirred overnight before the solid bisulfite addition product is added to a saturation sodium bicarbonate solution (25 ml.) and stirred for two hours at room temperature. The mixture is extracted with ether (2×50 ml.). The ether extracts are washed with brine (2×25 ml.), dried over $MgSO_4$ and evaporated in vacuo to give the (±)-6,7-dichloro-2,3-dihydro-5-(2-thenoyl)benzofuran-2-carboxaldehyde which melts at 162°-4° C.

Elemental analysis for $C_{14}H_8Cl_2O_3S$: Calc.: C, 51.39; H, 2.46; Found: C, 51.76; H, 2.83.

EXAMPLE 6

Where in Example 5 there is substituted for (±)methyl-6,7-dichloro-2,3-dihydro-5-(2-thenoyl)benzofuran-2-carboxylate an equimolar amount of
(±)methyl-6,7-dichloro-2,3-dihydro-5-(2-furoyl)benzofuran-2-carboxylate;
(±)methyl-6,7-dichloro-2,3-dihydro-5-(3-thenoyl)benzofuran-2-carboxylate;
(±)methyl-6,7-dichloro-2,3-dihydro-5-(5-methyl-2-thenoyl)-benzofuran-2-carboxylate;
(±)methyl-6,7-dichloro-2,3-dihydro-5-(5-methyl-2-furoyl)-benzofuran-2-carboxylate;
(±)methyl-2,3-dihydro-6,7-dimethyl-5-(2-thenoyl)benzofuran-2-carboxylate;
(±)methyl-2,3-dihydro-6,7-dimethyl-5-(2-furoyl)benzofuran-2-carboxylate;
(±)methyl-6-chloro-2,3-dihydro-7-methyl-5-(2-thenoyl)-benzofuran-2-carboxylate; or
(±)methyl-6-chloro-2,3-dihydro-7-methyl-5-(2-furoyl)benzofuran-2-carboxylate,
the following compounds of this invention are obtained respectively -
(±)6,7-dichloro-2,3-dihydro-5-(2-furoyl)benzofuran-2-carboxaldehyde;
(±)6,7-dichloro-2,3-dihydro-5-(3-thenoyl)benzofuran-2-caboxaldehyde;
(±)6,7-dichloro-2,3-dihydro-5-(5-methyl-2-thenoyl)-benzofuran-2-carboxaldehyde;
(±)6,7-dichloro-2,3-dihydro-5-(5-methyl-2-furoyl)benzofuran-2-carboxaldehyde;
(±)2,3-dihydro-6,7-dimethyl-5-(2-thenoyl)benzofuran-2-carboxaldehyde;
(±)2,3-dihydro-6,7-dimethyl-5-(2-furoyl)benzofuran-2-carboxaldehyde;
(±)6-chloro-2,3-dihydro-7-methyl-5-(2-thenoyl)benzofuran-2-carboxaldehyde;
(±)6-chloro-2,3-dihydro-7-methyl-5-(2-furoyl)benzofuran-2-carboxaldehyde.

EXAMPLE 7

(+)6,7-Dichloro-2,3-dihydro-5-(2-thenoyl)benzofuran-2-carboxaldehyde

Where in Example 5 there is substituted for (±)methyl-6,7-dichloro-2,3-dihydro-5-(2-thenoyl)benzofuran-2-carboxylate an equimolar amount of (+)methyl-6,7-dichloro-2,3-dihydro-5-(2-thenoyl)benzofuran-2-carboxylate there is produced an equivalent amount of (+)6,7-dichloro-2,3-dihydro-5-(2-thenoyl)benzofuran-2-carboxaldehyde.

EXAMPLE 8

(−)6,7-Dichloro-2,3-dihydro-5-(2-thenoyl)benzofuran-2-carboxaldehyde

Where in Example 5 there is substituted for (±)methyl-6,7-dichloro-2,3-dihydro-5-(2-thenoyl)benzofuran-2-carboxylate an equimolar amount of (−)methyl-6,7-dichloro-2,3-dihydro-5-(2-thenoyl)benzofuran-2-carboxylate there is produced an equivalent amount of (−)6,7-dichloro-2,3-dihydro-5-(2-thenoyl)benzofuran-2-carboxaldehyde.

EXAMPLE 9

6,7-Dichloro-2,3-dihydro-5-(2-thenoyl)benzofuran-2-carboxaldehyde ethyleneacetal A benzene mixture (250 ml.) containing 6,7-dichloro-2,3-dihydro-5-(2-thenoyl)benzofuran-2-carboxaldehyde (3.2 g., 0.01 mole), p-toluenesulfonic acid (0.2 g.) and ethyleneglycol (15 ml.) is heated under reflux for three hours. The water formed in the reaction is co-distilled with the benzene and is removed by a Dean-Stark apparatus. After three hours, the reaction mixture is cooled, washed twice with dilute sodium bicarbonate (2×50 ml.) once with water (50 ml.) and dried over magnesium sulfate. The solvent is evaporated under reduced pressure to give the 6,7-dichloro-2,3-dihydro-5-(2-thenoyl)-benzofuran-2-carboxaldehyde ethyleneacetal.

EXAMPLE 10

6,7-Dichloro-2,3-Dihydro-5-(2-thenoyl)benzofuran-2-carboxaldehyde dimethylacetal 6,7-Dichloro-2,3-dihydro-5-(2-thenoyl)benzofuran-2-carboxaldehyde (3.2 g., 0.01 mole) is dissolved in methanolic cesium chloride (25 ml., 0.4 M). Trimethylorthoformate (2.12 g., 0.02 mole) is added and the solution is stirred (magnetically) at room temperature for 30 minutes and then poured into aqueous sodium hydrogen carbonate (50 ml.). The mixture is extracted with ether (2×50 ml.). The ether extracts are combined, washed with brine (2×15 ml.), dried over $MgSO_4$ and distilled at reduced pressure to give the 6,7-dichloro-2,3-dihydro-5-(2-thenoyl)benzofuran-2-carboxaldehyde dimethylacetal.

EXAMPLE 11

2-Acetyl-6,7-dichloro-2,3-dihydro-5-(2-thenoyl)benzofuran

Step A:

6,7-Dichloro-2,3-dihydro-5-(2-thenoyl)benzofuran-2-carbonyl chloride

A benzene solution (25 ml.) containing 6,7-dichloro-2,3-dihydro-5-(2-thenoyl)benzofuran-2-carboxylic acid (3.4 g., 0.01 mole) and thionyl chloride (2 ml.) is refluxed for two hours. Evaporation of the benzene and excess thionyl chloride leaves the 6,7-dichloro-2,3-dihydro-5-(2-thenoyl)benzofuran-2-carbonyl chloride which is used in Step B without further purification.

Step B:

2-Acetyl-6,7-dichloro-2,3-dihydro-5-(2-thenoyl)-benzofuran

Cuprous iodide (5.7 g., 0.03 mole) is placed in a 250 ml. three-necked round-bottom flask equipped with a magnetic stirring bar, septum stopper, nitrogen inlet and $CaSO_4$ drying tube. The flask is flame dried while purging it with nitrogen. Diethyl ether (80 ml.) is added and the flask is cooled to 0° C. Methyl lithium (42.8 ml. of 1.4 M solution, 0.06 mole) is added to the stirred mixture. After ten minutes at 0° C. the temperature is lowered to −78° C. A cooled etheral solution (25 ml.) of 6,7-dichloro-2,3-dihydro-5-(2-thenoyl)benzofuran-2-carbonyl chloride (3.6 g., 0.01 mole) is added. After stirring 15 minutes at −b 78° C., the reaction is quenched by adding methanol (3.52 g., 0.011 mole). The reaction mixture is allowed to warm up to 25° C. and then is poured into 150 ml. of saturated aqueous ammonium chloride. The mixture is extracted with ether (3×50 ml.). The ether extracts are combined, dried over $MgSO_4$ and evaporated in vacuo to give 2-acetyl-6,7-dichloro-2,3-dihydro-5-(2-thenoyl)benzofuran.

EXAMPLE 12

2-Aminomethyl-6,7-dichloro-2,3-dihydro-5-(2-thenoyl)-benzofuran

A stirred solution containing 6,7-dichloro-2,3-dihydro-5-(2-thenoyl)benzofuran-2-carboxaldehyde (3.27 g., 0.01 mole) and ammonium acetate (6.16 g., 0.08 mole) in methanol (100 ml.) is treated with sodium cyanoborohydride (0.72 g., 0.0115 mole). After stirring 24 hours at 25° C., the reaction is acidified (pH below 2) with concentrated hydrochloric acid and the methanol is distilled at reduced pressure. The residue is stirred in water (25 ml.) for 15 minutes and then the mixture is extracted with ether (two 10 ml. portions). The aqueous layer is made basic (pH above 10) with potassium hydroxide pellets, saturated with sodium chloride and extracted with ether (two 10 ml. portions). The ether extract is dried over magnesium sulfate and the ether distilled under reduced pressure to give 2-amino-methyl-6,7-dichloro-2,3-dihydro-5-(2-thenoyl)benzofuran.

As mentioned previously, the novel compounds of this invention are diuretic and saluretic agents. When administered to patients in therapeutic dosages in conventional vehicles, the instant products effectively reduce the amount of sodium and chloride ions in the body, lower dangerous excesses of fluid levels to acceptable levels and in general, alleviate conditions usually associated with edema or fluid retention and hypertension.

Also as mentioned previously, these compounds are able to maintain the uric acid concentration in the blood at pretreatment levels or even cause a decrease in uric acid concentration. The presence of excess uric acid in the blood can lead to crystallization of uric acid and uric acid salts in the joints causing gout. In addition hyperuricemia in conjunction with hyperlipidemia has been implicated in increasing the risk of sustaining cardiovascular heart disease.

The compounds of this invention can be administered to patients (both animal and human) as the racemic form, as either enantiomer or in a wide variety of mixtures of various ratios of the two enantiomers, each of which may be given in any of a variety of therapeutic dosages in conventional vehicles, as for example, by oral administration in the form of a tablet or by intravenous injection. In addition, the compounds may be formulated into suppositories or as a salve for topical administration or they may be administered sublinqually. Also the daily dosage of the products may be varied over a wide range as for example, in the form of scored tablets containing 0.25, 1, 5, 10, 25, 50, 100, 150, 200, 250 and 500 milligrams of the active ingredient for the symptomatic adjustment of the dosage to the patient to be treated. These dosages are well below the toxic or lethal dose of the products.

A suitable unit dosage form of the product of this invention can be administered by mixing 50 mg. of a dihydrobenzofuran of the present invention with 149 mg. of lactose and 1 mg. of magnesium stearate and placing the 200 mg. mixture into a No. 1 gelatin capsule. Similarly by employing more of the active ingredient and less lactose, other dosage forms can be put up in No. 1 gelatin capsules and should it be necessary to mix more than 200 mg. of ingredients together larger capsules may be employed. Compressed tablets, pills or other desired unit dosages can be prepared to incorporate the compounds of this invention by conventional methods and if desired can be made up as elixirs or as injectable solutions by methods well known to pharmacists.

An effective amount of the product is ordinarily supplied at a unit dosage level of from about 0.003 mg. to about 10 mg./kg. of body weight of the patient. Preferably the range is from about 0.01 mg. to about 1.5 mg./kg. with a most preferred dose being about 0.07 to 0.35 mg./kg. of body weight. The unit dose can be administered as infrequently as twice per week to as frequently as 3 times per day.

It is also within the scope of this invention to combine two or more of the compounds of this invention into a unit dosage form or to combine one or more of the compounds of this invention with other known diuretics and saluretics or with other desired therapeutic and/or nutrive agents in dosage unit form.

The present invention embraces such compositions administration to patients, preferably by oral administration, wherein the potassium conserving diuretic, N-amidino-b 3,5-diamino-6-chloropyrazinecaroxamide hydrochloride, hereinafter referred to as amiloride hydrochloride is present as a physical mixture in combination with the dihydrobenzofurans of the present invention. The present invention embraces compositions wherein the molar ratio of the dihydrobenzofuran to amiloride hydrochloride ranges from about 50:1 to 1:1. The preferred ratios of the dihydrobenzofuran to amiloride hydrochloride ranges from 25:1 to 1:1.

EXAMPLE 13

Dry-filled capsules containing 50 mg. of active ingredients per capsule

|  | Per Capsule |
|---|---|
| (±)6,7-Dichloro-2,3-dihydro-5-(2-thenoyl)benzofuran-2-carboxaldehyde | 50 mg. |
| Lactose | 149 mg. |
| Magnesium stearate | 1 mg. |
| Capsule (Size No. 1) | 200 mg. |

The (±)6,7-dichloro-2,3-dihydro-5-(2-thenoyl)-benzofuran-2-carboxaldehyde is reduced to a No. 60 powder and then lactose and magnesium stearate are passed through a No. 60 bolting cloth unto the powder and the combined ingredients admixed for 10 minutes and then filled into a No. 1 dry gelatin capsule.

Similarly dry filled capsules can be prepared by replacing the active ingredient of the above example by a molar equivalent amount of any of the other novel compounds of this invention.

EXAMPLES 14–16

Following the procedure for combining the ingredients as described in Example 13, the following dry filled capsules can be prepared. Also dry filled capsules can be prepared by replacing the benzofuran active ingredient of the above examples by a molar equivalent of any of the other compounds of this invention.

EXAMPLE 14

Dry-Filled capsules containing 25 mg. of active ingredient per capsule

|  | Per capsule |
|---|---|
| (+)6,7-Dichloro-2,3-dihydro-5-(2- | |

-continued

| | Per capsule |
|---|---|
| thenoyl)benzofuran-2-carboxaldehyde | 25 mg. |
| Lactose | 174 mg. |
| Magnesium stearate | 1 mg. |
| Capsule (Size No. 1) | 200 mg. |

EXAMPLE 15

Dry-Filled capsules containing 75 mg. of active ingredients per capsule

| | Per capsule |
|---|---|
| (+)6,7-dichloro-2,3-dihydro-5-2-thenoyl)benzolfuran-2-carboxaldehyde | 25 mg. |
| (−)(6,7-dichloro-2,3-dihydro-5-(2-thenoyl)benzofuran-2-carboxaldehyde | 50 mg. |
| lactose | 124 mg. |
| Magnesium stearate | 1 mg. |
| Capsule (Size No. 1) | 200 mg. |

EXAMPLE 16

Dry-filled capsules containing 25 mg. of dihydrobenzofuran and 5 mg. of amiloride hydrochloride dihydrate per capsule

| | Per capsule |
|---|---|
| (±)6,7-dichloro-2,3-dihydro-5-(2-thenoyl)benzofuran-2-carboxaldehyde | 25 mg. |
| N-amidino-3,5-diamino-6-chloropyrazine-carboxamide hydrochloride dihydrate | 5 mg. |
| Lactose | 169 mg. |
| Magnesium Stearate | 1 mg. |
| Capsule (Size No. 1) | 200 mg. |

What is claimed is:

1. A compound of the formula:

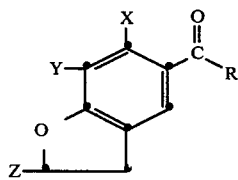

wherein

X is halo or methyl;

Y is halo, methyl or hydrogen;

X and Y can be combined to form a hydrocarbylene radical of from 3 to 4 carbon atoms;

R is selected from the group consisting of 2-thienyl, 3-thienyl, 5-methyl-2-thienyl, 1,2,5-thiadiazolyl, 3-methyl-1,2,5-thiadiazolyl, 2-furyl, 5-methyl-2-furyl, phenyl, p-methoxyphenyl, p-chlorophenyl, benzyl and p-chlorobenzyl and Z is acetyl, aminomethyl, formyl or hydroxymethyl.

2. The compound of claim 1 wherein X and Y are both chloro.

3. A compound of claim 1 wherein X and Y are chloro and R is 2-thienyl, 3-thienyl, 5-methyl-2-thienyl, 2-furyl, 3-furyl or 5-methyl-2-furyl and Z is formyl or hydroxymethyl.

4. The (+) and (−) isomers of the compound of claim 2.

5. The compound of claim 1 wherein X and Y are chloro, R is 2-thienyl and Z is hydroxymethyl thus forming 6,7-dichloro-2,3-dihydro-2-hydroxymethyl-5-(2-thenoyl)benzofuran.

6. The (+) enantiomer of the compound of claim 5.

7. The (−) enantiomer of the compound of claim 5.

8. A mixture of 1 part (+) enantiomer of the compound of claim 5 with 2 to 4 parts of the (−) enantiomer of the compound of claim 5.

9. The compound of claim 1 wherein X and Y are chloro, R is 2-thienyl and Z is formyl thus forming 2,3-dihydro-6,7-dichloro-2-carboxaldehyde-5-(2-thenoyl)benzofuran.

10. A pharmaceutical useful in the treatment of edema, hypertension, congestive heart failure, and the like composition comprising a therapeutically effect amount of a compound of the formula:

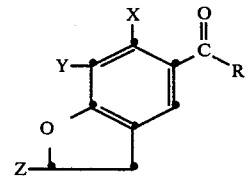

wherein

X is halo or methyl;

Y is halo, methyl or hydrogen;

X and Y can be combined to form a hydrocarbylene radical of from 3 to 4 carbon atoms;

R is selected from the group consisting of 2-thienyl, 3-thienyl, 5-methyl-2-thienyl, 1,2,5-thiadiazolyl, 3-methyl-1,2,5-thiadiazolyl, 2-furyl, 3-furyl, 5-methyl-2-furyl, phenyl, p-methoxyphenyl, p-chlorophenyl, benzyl and p-chlorobenzyl and Z is acetyl, aminomethyl, formyl or hydroxy methyl.

11. A method of treatment of edema associated with hypertension comprising the administration to a patient of from 0.01 mg. to 10 mg./kg. of body weight of the patient of a compound having the formula:

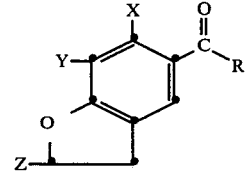

wherein

X is halo or methyl;

Y is halo, methyl or hydrogen;

X and Y can be combined to form a hydrocarbylene radical of from 3 to 4 carbon atoms;

R is selected from the group consisting of 2-thienyl, 3-thienyl, 5-methyl-2-thienyl, 1,2,5-thiadiazolyl, 3-methyl-1,2,5-thiadiazolyl, 2-furyl, 3-furyl, 5-methyl-2-furyl, phenyl, p-methoxyphenyl, p-chlorophenyl, benzyl and p-chlorobenzyl and Z is acetyl, aminomethyl, formyl or hydroxymethyl.

* * * * *